(12) United States Patent
Tanimoto et al.

(10) Patent No.: US 7,646,846 B2
(45) Date of Patent: Jan. 12, 2010

(54) METHOD FOR EVALUATING PRESS-FORMABILITY OF GALVANIZED STEEL SHEET

(75) Inventors: Wataru Tanimoto, Tokyo (JP); Hisato Noro, Tokyo (JP)

(73) Assignee: JFE Steel Corporation (JP)

(*) Notice: Subject to any disclaimer, the term of this patent is extended or adjusted under 35 U.S.C. 154(b) by 46 days.

(21) Appl. No.: 11/989,391

(22) PCT Filed: Sep. 22, 2005

(86) PCT No.: PCT/JP2005/018066

§ 371 (c)(1),
(2), (4) Date: Jan. 25, 2008

(87) PCT Pub. No.: WO2007/034570

PCT Pub. Date: Mar. 29, 2007

(65) Prior Publication Data

US 2009/0122957 A1     May 14, 2009

(51) Int. Cl.
*G01N 23/223* (2006.01)
(52) U.S. Cl. .................. 378/50; 378/44; 378/45; 378/46; 378/48; 378/49
(58) Field of Classification Search .......... 378/44, 378/45, 46, 48, 49, 50
See application file for complete search history.

(56) References Cited

U.S. PATENT DOCUMENTS 4,129,778 A * 12/1978 Inoue et al. ............... 378/50

(Continued)

FOREIGN PATENT DOCUMENTS

EP        0 348 574     1/1990

(Continued)

OTHER PUBLICATIONS

C. Carpanese et al., "Study on deposition kinetics of high-K materials by X-ray fluorescence techniques", Spectrochimica Acta Part B, vol. 59, Jul. 19, 2004 pp. 1183 to 1187.

(Continued)

*Primary Examiner*—Allen C. Ho
(74) *Attorney, Agent, or Firm*—DLA Piper LLP (US)

(57) ABSTRACT

The press formability of a galvanized steel sheet including an oxide film, which has a thickness of 10 nm to 100 nm, as a surface layer is nondestructively speedily evaluated. A specific method for solving problems is characterized by including the steps of irradiating X-rays to a galvanized steel sheet, dispersing a fluorescent X-ray, which is excited and emitted in the applying, with an analyzing crystal exhibiting the difference in diffraction angle between a primary oxygen $K\alpha$ x-ray and a secondary zinc $L\beta$ x-ray of 2 degrees or more, detecting the X-ray, which is dispersed in the dispersing and which mainly contains the primary oxygen $K\alpha$ x-ray, with a detector, separating an X-ray at an energy level within the range of ±25% to ±75% relative to the reference (100%) that is the energy level of the primary oxygen $K\alpha$ x-ray from the X-ray, which is detected in the detecting and which mainly contains the primary oxygen $K\alpha$ x-ray, by adjusting the window width of a pulse-height analyzer, measuring the intensity of the X-ray separated in the separating, and evaluating the press formability of the galvanized steel sheet on the basis of the intensity of the X-ray measured in the measuring.

4 Claims, 5 Drawing Sheets

U.S. PATENT DOCUMENTS

| | | | | |
|---|---|---|---|---|
| 4,162,528 | A * | 7/1979 | Maldonado et al. | 702/172 |
| 4,208,581 | A * | 6/1980 | Kaneko | 378/50 |
| 4,764,945 | A * | 8/1988 | Abe | 378/50 |
| 5,081,658 | A * | 1/1992 | Imai et al. | 378/45 |
| 5,113,421 | A * | 5/1992 | Gignoux et al. | 378/50 |
| 5,187,727 | A * | 2/1993 | Vogler et al. | 378/50 |
| 5,325,416 | A * | 6/1994 | Saito et al. | 378/50 |
| 6,173,036 | B1 * | 1/2001 | Hossain et al. | 378/45 |
| 6,310,935 | B1 | 10/2001 | Kuwabara | |
| 6,349,128 | B1 * | 2/2002 | Nelson | 378/44 |
| 6,816,570 | B2 * | 11/2004 | Janik et al. | 378/50 |
| 7,356,114 | B2 * | 4/2008 | Kataoka et al. | 378/44 |
| 7,450,685 | B2 * | 11/2008 | Kataoka et al. | 378/45 |

FOREIGN PATENT DOCUMENTS

| | | |
|---|---|---|
| JP | 53-60332 | 5/1978 |
| JP | 2010144 | 1/1990 |
| JP | 2-190483 | 7/1990 |
| JP | 3-191093 | 8/1991 |
| JP | 4-88196 | 3/1992 |
| JP | 10-113724 | 5/1998 |
| JP | 2001041909 | 2/2001 |
| JP | 2003-136151 | 5/2003 |
| JP | 2004-3004 | 1/2004 |
| JP | 2005-248262 | 9/2005 |

OTHER PUBLICATIONS

D. M. Barrus, and R. L. Blake, "Comparison of crystals for oxygen analysis", X-ray Spectrometry, vol. 10, No. 1, Jan. 1981, pp. 48 to 51.
Non-patent document 1, "Keikou X sen Bunsekihou no Tebiki (Guide to Flourescent X ray Analysis)", Rigaku Industrial Corp. issued in Jul. 1993, p. 23.

* cited by examiner

METHOD FOR EVALUATING PRESS-FORMABILITY OF GALVANIZED STEEL SHEET

RELATED APPLICATION

This is a §371/continuation of International Application No. PCT/JP2005/018066, with an international filing date of Sep. 22, 2005 (WO 2007/034570 A1, published Mar. 29, 2007).

TECHNICAL FIELD

This disclosure relates to speedily evaluating the press formability of a galvanized steel sheet by nondestructively speedily measuring the amount of an oxide film which is formed on the galvanized steel sheet and which has a thickness of 10 nm to 100 nm.

BACKGROUND

In the fields of iron and steel products, semiconductor products, display products, and the like, surface films having thicknesses of a few tens to a few hundreds of nanometers may be controlling factors of product characteristics. In the field of iron and steel products, surface thin films having thicknesses of a few tens to a few hundreds of nanometers may be controlling factors for press formability of the products. In recent years, many of steel sheets to be used for automobiles and household electrical appliances are subjected to galvanization from the viewpoint of high corrosion resistance. However, in the case where a hard forming part is produced by press-forming of the plated steel sheet, there is a problem in that press-cracking easily occurs at a site, which undergoes severe forming, in the steel sheet. In a known method for improving the press formability of the galvanized steel sheet by using a high-viscosity lubricating oil during pressing, there is a problem in that variations occur in downstream steps, e.g., a conversion treatment and painting, unless a degreasing process is enhanced.

A method, in which a coating taking a lubricating action is formed on a surface of a plating layer, is known as a method for decreasing the above-described fear in the downstream steps. For example, Japanese Unexamined Patent Application Publication Nos. 53-60332 (page 1), 2-190483 (page 1) and 2004-3004 (page 2) disclose a technology for improving the weldability or the formability by subjecting a surface of the galvanized steel sheet to an electric field treatment, a dip treatment, an oxidation treatment after coating, or a heat treatment so as to form an oxide film mainly containing a zinc oxide. Japanese Unexamined Patent Application Publication No. 4-88196 (page 1) discloses a technology for improving the press formability and the conversion treatment performance by dipping a galvanized steel sheet in an aqueous solution containing 5 to 60 g/L of sodium phosphate and exhibiting a pH of 2 to 6, performing an electric field treatment, or applying the above-described aqueous solution so as to form an oxide film mainly containing a phosphorous oxide on a surface of the plated steel sheet. Japanese Unexamined Patent Application Publication No. 3-191093 (page 1) discloses a technology for improving the press formability and the conversion treatment performance by performing an electric field treatment, a dip treatment, a coating treatment, an oxidation treatment after coating, or a heat treatment so as to form Ni oxide on a surface of a galvanized steel sheet.

The most direct manner for evaluating the press formability of the plated steel sheet is, for example, to perform pressing in practice with a full-size test machine imitating a mold to be used in a practical automobile part production and evaluate on the basis of an occurrence of cracking or wrinkling due to the pressing. However, this testing method requires a full-size test piece, large facilities, and efforts. Therefore, a sliding property testing method has been put into practical use as a method for evaluating the sliding property which is an important factor of the press formability. Examples of such a sliding test disclosed include a method in which one surface or both surfaces of a test piece is pressed against a die, the test piece is pulled out, the friction coefficient is determined from the pull-out resistance of the die and the test piece at this time, and the press formability is evaluated on the basis of the friction coefficient (refer to Japanese Unexamined Patent Application Publication No. 2004-3004 (page 2), for example), and a method in which the press formability is evaluated by an evaluation method based on the contact sliding of a metal body over a plated steel sheet (refer to Japanese Unexamined Patent Application Publication No. 2003-136151 (page 2), for example).

On the other hand, as is clear from the above-described known technologies, the press formability is controlled by the thickness of the lubricating film formed as the surface layer of the plated steel sheet. Therefore, the press formability can also be evaluated on the basis of the film thickness. In particular, in the case where an oxygen-containing film (oxide film) taking a lubricating action is formed on a surface of the plating layer, the sliding property is changed significantly depending on the oxide film thickness. Consequently, the sliding property can be evaluated by measuring the thickness of the oxide film, and it is possible to use as a simple alternative index of the press formability.

The known technologies for measuring the oxide film thickness are as described below:

(1) A method in which the information in the depth direction is measured by combining a surface analysis technique, e.g., Auger electron spectroscopy or X-ray photoelectron spectroscopy, and ion etching;

(2) A method in which a sample showing a cross section is prepared and observed with a transmission electron microscope from a film thickness direction; and (3) An optical technique, e.g., ellipsometry, by using an interference effect of light in a thin film.

SUMMARY

In the sliding test, since a die end portion is directly brought into contact with a sample surface, the die end portion continuously varies during the test. To ensure the reproducibility of evaluation, it is important to equalize areas, shapes, cleanliness, and the like of die end portions. If the uniformity is insufficient, errors occur in the evaluation. Consequently, much effort is required for the maintenance of the die end portion to perform highly accurate evaluation. Furthermore, a destruction test is performed basically, it is impossible to remeasure the same sample. Therefore, the remeasurement is forced to perform on the assumption that the measurement sample cut from the product and a sample in the vicinity of the measurement sample are equivalent to each other, so that the remeasurement has a problem.

A hot-dip galvanized steel sheet has an effect of improving the press formability, even when the thickness of the oxide film on the plating surface is at a level of a few nanometers. As is disclosed in Japanese Unexamined Patent Application Publication No. 2004-3004 (page 2) and the like, in particular, the improvement effect becomes significant when the film thickness becomes 10 nm or more. Therefore, if the thickness of the oxide film on the plating surface can be measured speedily, the yield of the product having excellent press formability can be improved by feeding back the measurement results to a production process, and the quality control of the product can be performed by using the measurement results for judging the shipment.

Problems in the known methods for measuring the oxide film thickness will be described below. Among the methods which are described in the above-described items (1) to (3) and which can be used for evaluating the thickness of a very thin oxide film, the methods of items (1) and (2) require a long time for measurement or sample preparation, and are very difficult to use for judging the shipment, let alone feed back to the process.

Regarding the method of item. (1), since the sample needs to be measured in an ultrahigh vacuum, evacuation takes a few tens of minutes to a few hours even when an apparatus provided with a spare evacuation apparatus is used. Furthermore, since the oxide film thickness is measured by repeating ion etching having a known etching rate, the measurement takes at least a few hours on a sample basis. Regarding the method of item (2), preparation of one sample takes at least a half day, a transmission electron microscope observation of the prepared sample further takes about one hour, and development of the resulting electron micrograph further takes a few hours. Therefore, an evaluation of the film thickness takes at least about one day on a sample basis.

The optical technique of item (3) by using an interference effect is suitable for evaluating the film thickness of a sample having a thin film to be evaluated on an optically flat surface and substrate, such as a thermally grown oxide film formed on a silicon wafer, and can also be used for on-line measurement. However, for example, in the case where uneven surface resulting from skin-pass rolling or fine uneven surface resulting from alloying reaction is present on a substrate plated steel sheet as in the alloyed hot-dip galvanized steel sheet, it is difficult to ensure the measurement accuracy of the film thickness.

As described above, under the present circumstances, there is no known technology that can measure the thickness of a very thin oxide film formed on a hot-dip galvanized steel sheet at a speed not hindering the shipment.

Thus, it could be advantageous to provide methods for nondestructively speedily measuring the thickness of an oxide film which is formed on a galvanized steel sheet and which has a thickness of 10 nm to 100 nm and, thereby, speedily evaluating the press formability of the plated steel sheet provided with the oxide film on the basis of the measured oxide film thickness.

We found that the fluorescent X-ray analysis performed under a specific condition was able to lead to nondestructive, speedy measurement of the thickness of the oxide film which was formed on a galvanized steel sheet and which had a thickness of a few tens of nanometers, and the press formability was able to be speedily evaluated by using the measurement values. This disclosure has been made on the basis of this finding, and the gist thereof is as described below.

A method for evaluating the press formability of a galvanized steel sheet according to a first aspect is characterized by including the steps of irradiating X-rays to a galvanized steel sheet which is a sample to be measured; dispersing a fluorescent X-ray, which is excited and emitted in the above-described applying, with an analyzing crystal exhibiting the difference in diffraction angle between a primary oxygen Kα x-ray and a secondary zinc Lβ x-ray of 2 degrees or more; detecting the X-ray, which is dispersed in the above-described dispersing and which mainly contains the oxygen Kα x-ray, with a detector; separating an X-ray at an energy level within the range of ±25% to ±75% relative to the reference, 100%, that is the energy level of the primary oxygen Kα x-ray from the X-ray, which is detected in the above-described detecting and which mainly contains the primary oxygen Kα x-ray, by adjusting the window width of a pulse-height analyzer; measuring the intensity of the X-ray separated in the above-described separating; and evaluating the press formability of the galvanized steel sheet on the basis of the intensity of the X-ray measured in the above-described measuring.

According to a second aspect, in the method for evaluating the press formability of a galvanized steel sheet according to the first aspect, a calibration curve representing the relationship between the intensity of primary oxygen Kα x-ray and the oxide film thickness is prepared by using silicon oxide films with known thickness formed on mirror polished silicon wafers, the thickness of the oxide film formed on the galvanized steel sheet is calculated by using the calibration curve from the intensity of the X-ray measured in the above-described measuring, and the press formability of the galvanized steel sheet is evaluated on the basis of the calculated film thickness.

The thickness of the oxide film, which is formed as the surface layer of the galvanized steel sheet and which has a thickness of 10 nm to 100 nm, can be nondestructively speedily measured. Furthermore, the level of the press formability of the galvanized steel sheet can be speedily evaluated on the basis of the measured oxide film thickness.

DETAILED DESCRIPTION

Figure 1:
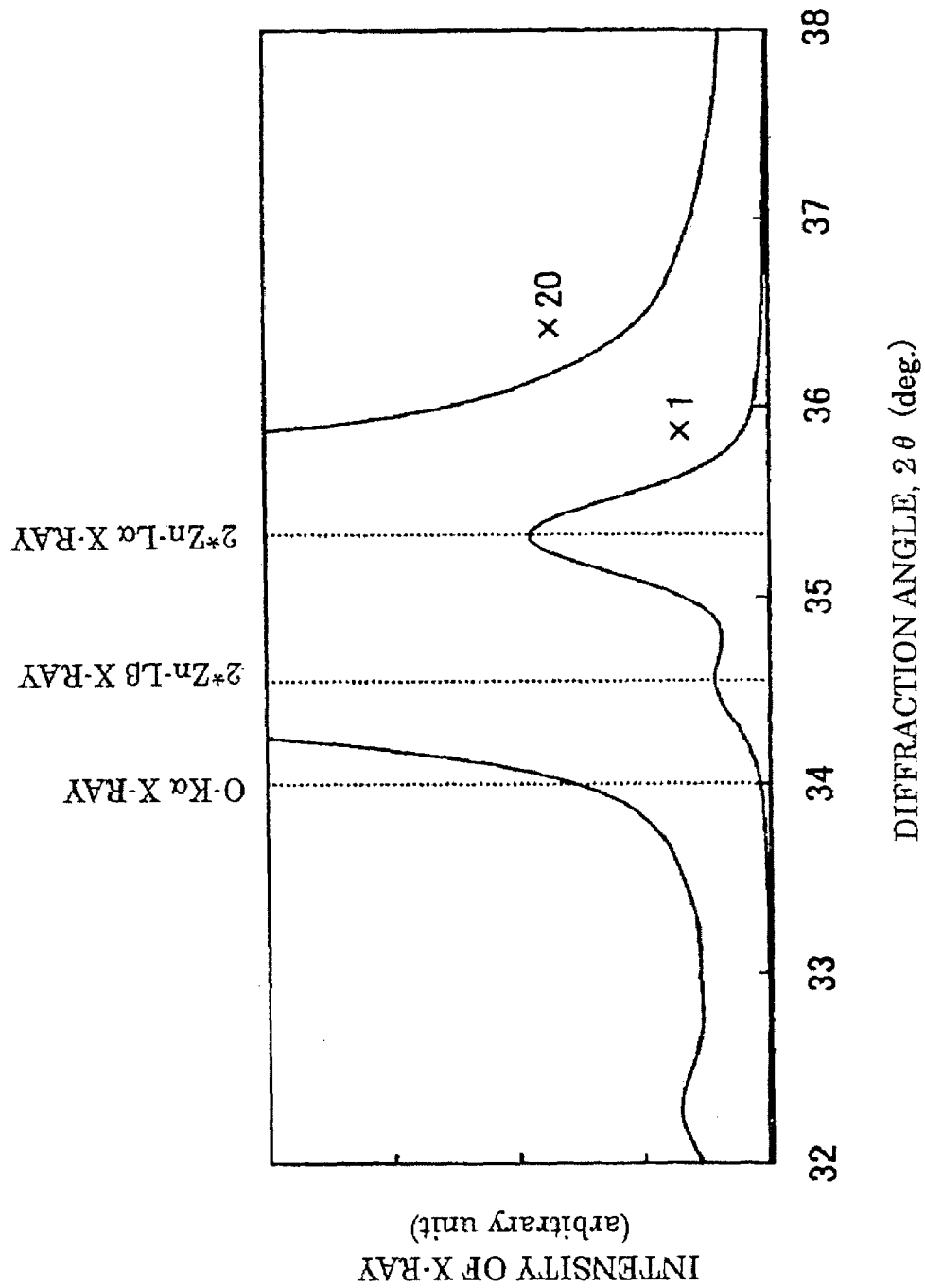
FIG. 1 is a fluorescent X-ray spectrum in the vicinity of O-Kα x-ray by using LMD (artificial multilayer film).

We found that the fluorescent X-ray analysis (hereafter abbreviated as "FX method") performed under a specific condition was able to lead to nondestructive, speedy measurement of a few tens of nanometers of thickness of the oxide film formed on a galvanized steel sheet, and the press formability was able to be speedily evaluated.

The oxide film may be microscopically discontinuous oxygen-containing substances. In that case, the film thickness refers to a thickness of a dense uniform film converted from the above-described substances.

In the FX method, high-intensity X-rays are generated from an Rh tube or the like, and are irradiated to a sample to be measured. In this analytical method, the fluorescent X-ray excited and emitted by the X-ray application is dispersed by using an analyzing crystal and is allowed to pass through a pulse-height analyzer, the intensity of characteristic X-ray of a desired element is measured, and the identification of the substance and the composition analysis are performed on the basis of the intensity of the X-ray.

The analyzing crystal can effectively reflect merely the fluorescent X-ray with a specific wavelength based on the Bragg condition determined from the incident angle of the fluorescent X-ray emitted from a sample and the interplanar spacing of the analyzing crystal. Therefore, the FX method can speedily measure the intensity of characteristic X-ray of the desired element.

The analyzing crystals include a plurality of crystals having X-ray reflection efficiencies different from each other depending on the wavelengths. Usually, they are used properly in accordance with the element to be analyzed (refer to Japanese Unexamined Patent Application Publication No. 53-60332 (page 1), for example).

For the analysis of oxygen by the FX method, an analyzing crystal of LMD (artificial multilayer film), TAP (thallium acid phthalate), or RAP (rubidium acid phthalate) can be used. However, in general, LMD is used as the analyzing crystal in the analysis of oxygen by the FX method on the ground as described below:
(i) The wavelength of characteristic X-ray of oxygen is close to the higher limit of the effective wavelength of TAP and PAP and, therefore, the reflection efficiency is low.
(ii) The use of LMD leads to a higher reflection efficiency of characteristic X-ray of oxygen, that is, a higher measurement intensity, so that the measurement accuracy is improved.

However, according to our analysis of oxygen contained in an oxide film formed on a galvanized steel sheet by using the LMD analyzing crystal, the following problem was made clear. That is, large amounts of secondary zinc Lα x-ray and Lβ x-ray (hereafter abbreviated as 2*Zn-Lα x-ray and 2*Zn-Lβ x-ray, respectively) of characteristic X-ray of zinc emitted from substrate zinc were detected in the vicinity of the detection position (detection angle) of primary oxygen Kα x-ray (hereafter abbreviated as O-Kα x-ray) of characteristic X-ray of oxygen and, in particular, the 2*Zn-Lβ x-ray almost entirely overlapped the O-Kα x-ray, so that the intensity of the O-Kα x-ray was not able to be measured properly.

It is a previously known phenomena that a detection position of the characteristic X-ray of a desired element and a higher order x-ray of another element overlap each other. At present, this is usually dealt with by the use of a diffraction line causing no overlap even if the intensity of- the diffraction line decreases or by techniques, e.g., overlap correction. However, regarding the thin oxide film formed on the zinc-containing substrate, the influence of overlap is significant. Therefore, the analysis of the oxide film thickness cannot be performed accurately by the known technique in this situation.

FIG. 1 shows a fluorescent X-ray spectrum in the wavelength region containing the O-Kα x-ray obtained by using LMD analyzing crystal regarding a sample of a galvanized steel sheet (alloyed hot-dip galvanized steel sheet) provided with an oxide film of 37 nm on a plating surface. As shown in FIG. 1, the O-Kα x-ray and the 2*Zn-Lβ x-ray are a mere about 0.5 degrees apart in diffraction angle, and the intensities of 2*Zn-Lα and 2*Zn-Lβ x-rays are drastically larger than the intensity of the O-Kα x-ray. Consequently, at the diffraction angle of the O-Kα x-ray, the peak of the O-Kα x-ray is hidden behind the peak of the 2*Zn-Lβ x-ray and is not observed at all (the spectrum indicated by "×1" in FIG. 1). In FIG. 1, the spectrum with the vertical axis magnified by 20 times (the spectrum indicated by "×20" in FIG. 1) is further shown to observe the peak of O-Kα x-ray in detail. However, the peak position of the O-Kα x-ray is in a tail of the peak of the 2*Zn-Lβ x-ray. As a result, the peak of the O-Kα x-ray cannot be observed at all. In this situation, the measurement of the intensity of O-Kα x-ray and the evaluation of the press formability based on the measurement cannot be performed.

Therefore, in the analysis of oxygen contained in the oxide film on the galvanized steel sheet, separation of the O-Kα x-ray and the 2*Zn-Lβ x-ray from the substrate is basically important.

We conducted intensive research and, as a result, found that the O-Kα x-ray and the 2*Zn-Lβ x-ray from the substrate were able to be separated and the amount of oxygen contained in the oxide film on the galvanized steel sheet was able to be accurately measured by satisfying the following configuration.

Figure 2:
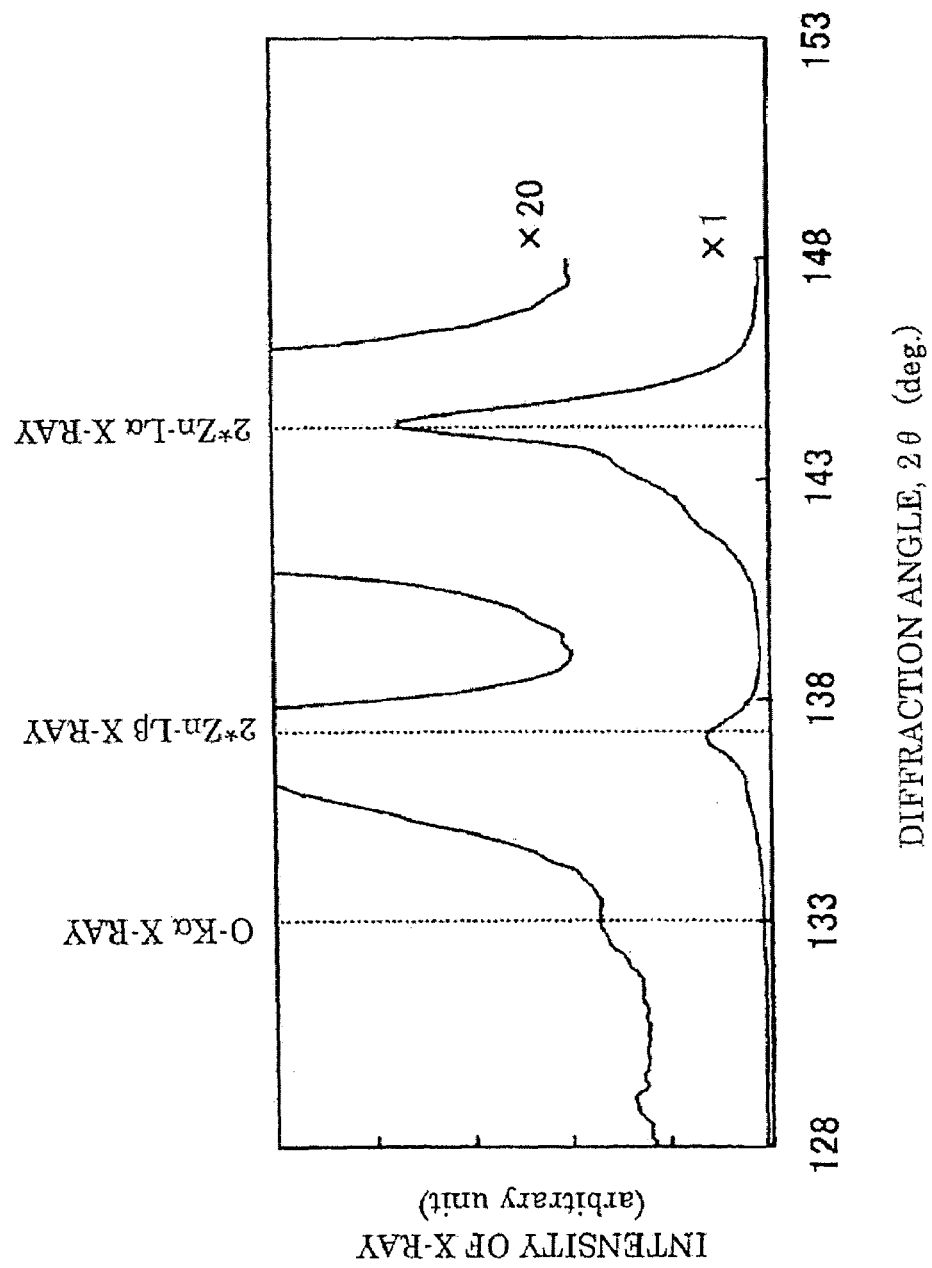
FIG. 2 is a fluorescent X-ray spectrum in the vicinity of O-Kα x-ray by using TAP (thallium acid phthalate).

FIG. 2 shows the result of measurement of a fluorescent X-ray spectrum of the same sample as the sample described above by using a TAP crystal exhibiting wavelength resolution higher than that of the LMD analyzing crystal. The O-Kα x-ray and the 2*Zn-Lβ x-ray are about 4.2 degrees apart in diffraction angle, and as is clear from the spectrum with the vertical axis magnified by 20 times (the spectrum indicated by "×20" in FIG. 2), the peak of O-Kα x-ray appears while being weak. It is clear from the above-described results that the peak of the O-Kα x-ray, which is not observed at all by using LMD, can be slightly observed by using the TAP analyzing crystal exhibiting high wavelength resolution.

Figure 3:
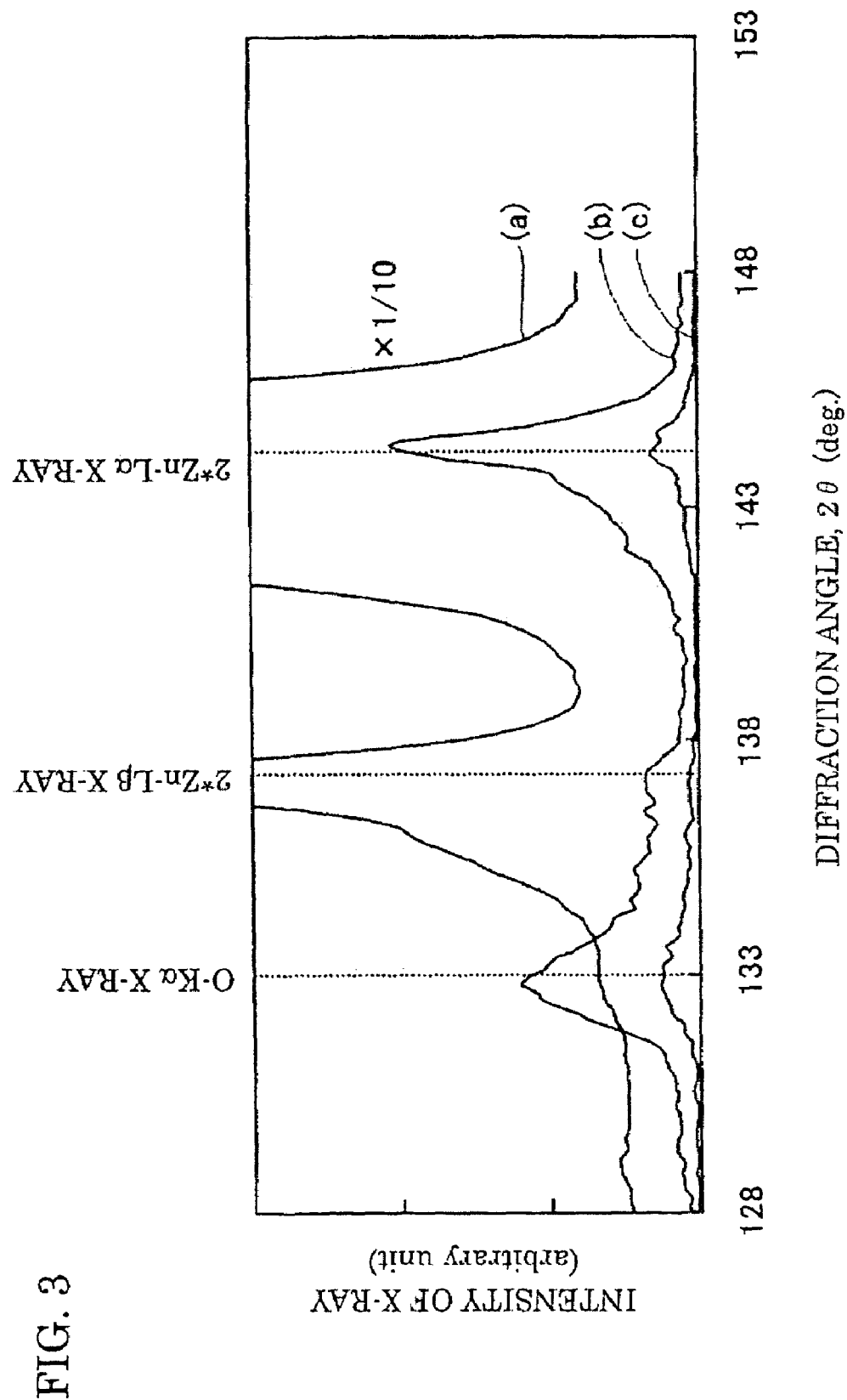
FIG. 3 is a diagram showing changes in the X-ray spectrum when the window width of a pulse-height analyzer is changed, where (a) the window width is open, (b) the window width is proper, and (c) the window width is too small.

FIG. 3 shows changes in the X-ray profile when the window width of a pulse-height analyzer is changed. The window width will be described later. In the case (a), the window width is open, in the case (b), the window width is an optimum value, and in the case (c), the window width is small than the optimum value. The following facts are made clear from FIG. 3. In the case (a), merely a slight peak of O-Kα x-ray appears on the tail of the peak of 2*Zn-Lβ x-ray. In the case (b), a clear peak of O-Kα x-ray appears. As the window width of the pulse-height analyzer is made smaller than the window width in the open state, the peak of 2*Zn-Lβ x-ray becomes low, and the peak of O-Kα x-ray becomes clearly observed. However, if the window width becomes too small, the intensity of the peak of O-Kα x-ray itself attenuates, and unfavorably, the peak of O-Kα x-ray becomes obscure, as shown in the case (c).

As is clear from the above-described results, the peak of O-Kα x-ray is allowed to clearly appear by using the analyzing crystal exhibiting high wavelength resolution as the analyzing crystal and setting the window width of the pulse-height analyzer at an appropriate width.

The plating components of the galvanized steel sheet may include elements, e.g., iron, chromium, nickel, silicon, aluminum, magnesium, lead, antimony, tin, manganese, titanium, lithium, and copper, besides zinc. The type of the oxide film on the plating surface is not specifically limited.

To accurately measure the oxide film thickness, it is desirable that a sample of the galvanized steel sheet is cut into the size suitable for being placed on a sample holder of an FX apparatus (fluorescent X-ray analyzer) to be used for the measurement and contaminants adhered to the sample are removed in advance by ultrasonic cleaning for a few minutes with organic solvent based degreasing solution, e.g., toluene and ethanol.

As described above, in the measurement of the O-Kα x-ray of the oxide film on zinc, the 2*Zn-Lβ x-ray that appears in the vicinity of the detection position of the O-Kα x-ray in dispersion needs to be eliminated. For that purpose, it is necessary that the O-Kα x-ray and the 2*Zn-Lβ x-ray can be separated in dispersion. From this point of view, it is enough that the difference in refraction angle between the two x-rays is 2 degrees or more. The difference in refraction angles of a commonly used LMD is small and, therefore, the O-Kα x-ray and the 2*Zn-Lβ x-ray cannot be separated. The use of TAP exhibiting high wavelength resolution as the analyzing crystal can lead to appearance of the peak of O-Kα x-ray because the difference between the O-Kα x-ray and 2*Zn-Lβ x-ray is 4.2 degrees. However, as described above, the wavelength of the O-Kα x-ray is close to the higher limit of the effective wavelength of TAP and, therefore, there is a problem in that detection of the O-Kα x-ray is unstable.

It was noted that the peak of O-Kα x-ray was allowed to clearly appear by setting the window width of the pulse-height analyzer at an appropriate width and, on the basis of this finding, research was conducted on a method that was able to stably detect the O-Kα x-ray in the case where TAP was used as the analyzing crystal. The same sample was measured 5 times under different window width of the pulse-height analyzer. The standard deviation of obtained values was calculated as the repeatability ($\sigma$) by using the following equation:

$$\sigma = \sqrt{\frac{n\sum x^2 - (\sum x)^2}{n(n-1)}}.$$

The window width regulates the energy range of X-ray screened with the pulse-height analyzer. In the present specification, the window width B (%) refers to the fact that the energy level of the O-Kα x-ray is assumed to be a reference value (100%), X-rays having energy out of the range from [reference value (100%)−B/2 (%)] to [reference value (100%)+B/2(%)] are excluded and merely X-rays having energy within the range from [reference value (100%)−B/2 (%)] to [reference value (100%)+B/2(%)] are measured.

Figure 4:
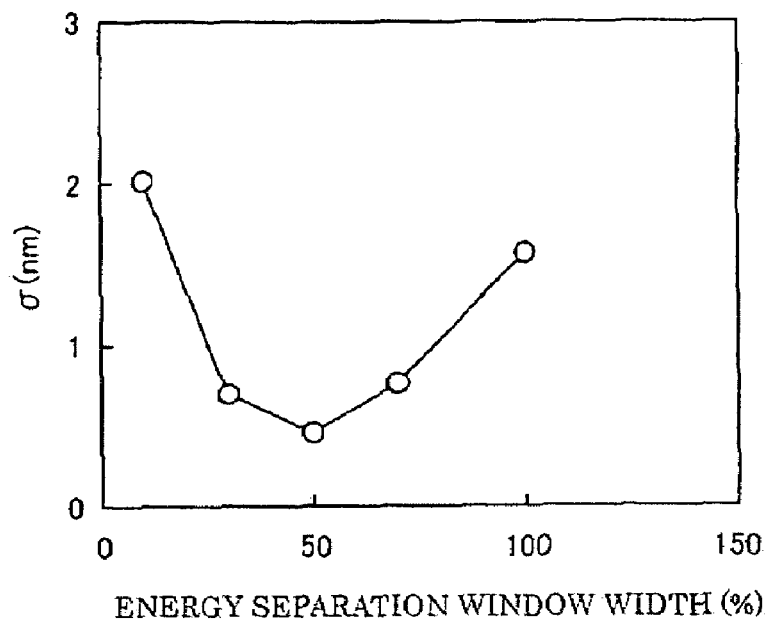
FIG. 4 is a diagram showing changes in analysis repeatability (σ) with the window width.

The obtained five times measurement and the value of $\sigma$ calculated from the measurement values are shown in Table 1. The relationship between the window width and the value of $\sigma$ is shown in FIG. 4.

TABLE 1

| Window width (%) | First time | Second time | Third time | Fourth time | Fifth time | Average | σ (nm) |
|---|---|---|---|---|---|---|---|
| 100 | 26.2 | 28.0 | 29.8 | 26.2 | 26.4 | 27.3 | 1.6 |
| 70 | 22.2 | 23.9 | 22.0 | 23.2 | 22.7 | 22.8 | 0.8 |
| 50 | 23.0 | 24.2 | 23.3 | 23.8 | 23.4 | 23.6 | 0.5 |
| 30 | 24.0 | 22.5 | 22.8 | 24.0 | 22.9 | 23.2 | 0.7 |
| 10 | 21.4 | 22.5 | 26.6 | 24.7 | 23.9 | 23.8 | 2.0 |

As is clear from these results, there is an optimum value of the window width. When the window width is 50%, that is, the energy of X-rays to be separated is within the range of ±25% of the reference value (100%) (within the range of 75% to 125% of the energy level of oxygen Kα x-ray), where the energy level of oxygen Kα x-ray is the reference value (100%), the measurement accuracy is the best, and the value of $\sigma$ at that time is 0.5 nm. When the window width is 50% or more, the measurement accuracy decreases, as the window width increases. This is because separation of merely the oxygen Kα x-ray becomes difficult. When the window width is 50% or less, the measurement accuracy decreases, as the window width decreases. This is because the amount of detection of O-Kα x-ray decrease and, thereby, the measurement accuracy decreases.

According to the above-described results, the optimum window width is 50%. However, the window width may be determined in accordance with the required measurement accuracy. For example, in the case where the press formability of a hot-dip galvanized steel sheet having an oxide film on a plating surface is evaluated, it is desirable that the value of $\sigma$ is 1 nm or less. From this point of view, it is specified that the window width is set within the range of ±25% to ±75% relative to the reference (100%), where the energy level of O-Kα x-ray is assumed to be the reference.

The X-ray separated with the pulse-height analyzer is subjected to a signal treatment, as in a manner generally performed, and is indicated as the intensity of X-ray. For example, the intensity of the X-ray separated with the pulse-height analyzer is integrated for a predetermined time with an integrator or the like. The integrated signal is converted to a digital signal with an A/D converter or the like, and is fed to a calculator. The calculator normalizes the fed signal into, for example, the intensity per second, and output as the intensity of O-Kα x-ray. The press formability of the galvanized steel sheet is evaluated on the basis of the intensity of O-Kα x-ray determined as described above.

It is desirable that the measurement time is determined in consideration of an allowable total measurement time and the relative variation. In general, statistical relative variation becomes the inverse of the square root of N, where N represents the number of counts measured. Therefore, for example, if 10,000 counts or more can be measured, the relative variation can be controlled at 1% or less. Based on such a concept, in general, it is practical that a measurement is performed within the range of a few seconds to a few tens of seconds per point.

In this manner, the oxygen content of the oxide film on the galvanized steel sheet surface can be accurately measured only on the condition that the analyzing crystal capable of separating the O-Kα x-ray and the 2*Zn-Lβ x-ray is used and the window condition of the pulse-height analyzer is specified to be an appropriate condition.

As described above, there is a correlation between the oxide film thickness and the press formability. In general, as the oxide film thickness increases, the press formability is improved. Consequently, there is a correlation between the oxygen content obtained from a film analysis and the press formability. In general, as the oxygen content increases, the press formability or the sliding property (friction coefficient) serving as an alternative index of the press formability is improved. Therefore, the press formability of the galvanized steel sheet can be evaluated by researching and determining the correlation between the oxygen content of the oxide film on the plating surface of the galvanized steel sheet and the press formability in advance and measuring the oxygen content of a sample, which is to be measured and which is taken from the galvanized steel sheet to be evaluated.

In the FX method, usually, a quantitative analysis is performed, in which a calibration curve is prepared by using a standard sample with known concentration, and a concentration of a sample with unknown concentration is calculated from the intensity of X-ray obtained from the sample with unknown concentration and the calibration curve. However, for the oxide film on the galvanized steel sheet, a standard sample with known film thickness is not always easily prepared. In this case, a commercially available sample, e.g., a silicon oxide film, which has a known film thickness and which is formed on a silicon wafer, is taken as a standard sample, the standard sample is measured together with an unknown sample and, thereby, the measurement results are easily standardized. A calibration curve representing the relationship between the intensity of O-Kα x-ray of the above-described standard sample and the oxide film thickness is prepared and, thereby, the oxide film thickness of an unknown sample can be indicated in terms of an oxide film thickness of the standard sample. Strictly, the silicon oxide film and the zinc based oxide film are different in the manufacturing method and the like, and if, for example, the densities or the like are different, an absolute thickness of the zinc based oxide film itself is not indicated. However, no problem occurs in practice because relative comparisons can be made by performing conversion to a film thickness in terms of silicon oxide film thickness at all times.

Alternatively, a threshold value of the oxygen content of the oxide film corresponding to the evaluation criterion of the press formability is determined in advance, the oxygen content obtained by the above-described measurement and the threshold value of the oxygen content corresponding to the evaluation criterion of the press formability are compared and, thereby, the level of the press formability of the galvanized steel sheet can be judged on the basis of whether the measurement value of the oxygen content is more than or equal to the threshold value corresponding to the evaluation criterion or not.

Alternatively, a threshold value of the oxide film thickness corresponding to the evaluation criterion of the press formability is determined in advance, the oxide film thickness obtained by the above-described measurement and the threshold value of the oxide film thickness corresponding to the evaluation criterion of the press formability are compared and, thereby, the level of the press formability of the galvanized steel sheet can be evaluated on the basis of whether the measurement value of the oxide film thickness is more than or equal to the threshold value corresponding to the evaluation criterion or not.

The above-described evaluation criteria may be two levels. For example, when the oxygen content is more than or equal to a predetermined threshold value, the evaluation result may be good, and when the oxygen content is less than the threshold value, the evaluation result may be no good. The evaluation levels may be three or more levels. For example, a plurality of good levels may be set in the above description, and a threshold value of the oxygen content corresponding to each level may be determined.

If the type of oxide is changed, the correlation between the oxide film thickness and the oxygen content and the threshold value of the oxygen content of the oxide film corresponding to the evaluation criterion of the press formability may be changed. Therefore, the above-described correlation is determined on a type of oxide basis.

The intensity of O-Kα x-ray is efficiently converted to the oxide film thickness through the use of a calibration curve prepared by using silicon oxide films with known thickness formed on mirror polished silicon wafers. Such silicon oxide films with known thickness are particularly favorably used, because these films are commercially available in the form of standard samples for the analysis in a depth direction in the surface analysis, e.g., Auger electron spectroscopy or X-ray photoelectron spectroscopy, and are easily available. Furthermore, calculation can be performed on the basis of the same standard sample as that of the known technology in which the film thickness is measured in combination of the surface analysis technique and the ion etching. Therefore, there is an advantage that the obtained result matches with the value based on the known technology, in spite of swiftness regarding the measurement time.

Figure 6:
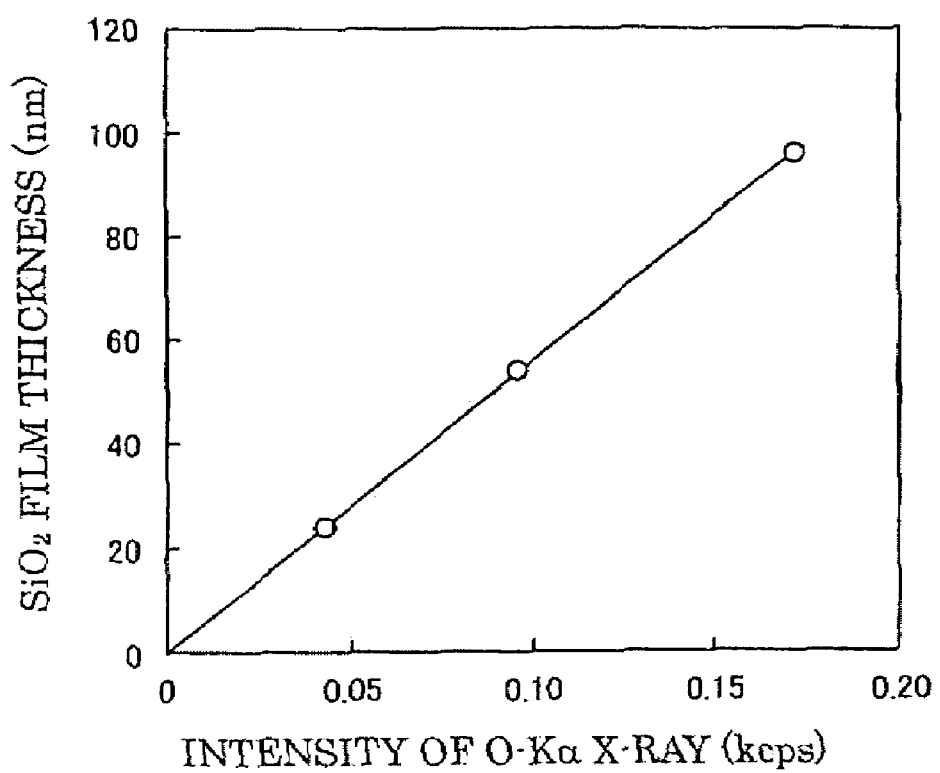
FIG. 6 is a diagram showing the relationship between the intensity of O-Kα x-ray measured by using silicon wafers provided with silicon oxide films and the $SiO_2$ film thickness.

FIG. 6 is a diagram showing the relationship between the intensity of O-Kα x-ray measured by using silicon wafers provided with silicon oxide films having thicknesses of 96 nm, 54 nm, and 24 nm and the $SiO_2$ film thickness. The line in the drawing indicates the linear regression equation determined on the basis of points of the above-described three samples and an origin point. It is possible to univocally convert the intensity of O-Kα x-ray obtained from the evaluation sample to the film thickness value by using the above-described relationship. The press formability may be evaluated on the basis of this film thickness value.

Since the silicon wafers provided with silicon oxide films with long-term stability are used as the standard samples, output of stable analysis values can be maintained, even when variations in the measurement intensity occur due to deterioration, fouling, or the like of an X-ray tube and a detector of the FX apparatus.

In the above-described description, TAP is used as the analyzing crystal. However, the analyzing crystal to be used is not limited to TAP. Any analyzing crystal may be used insofar as the analyzing crystal exhibits a difference in diffraction angle between the O-Kα x-ray and the 2*Zn-Lβ x-ray of 2 degrees or more.

The FX apparatus may be a commercially available apparatus, insofar as the apparatus is provided with, for example, a TAP analyzing crystal produced by Rigaku Industrial Corp., a proportional counter, and a pulse-height analyzer.

EXAMPLE 1

Our methods will be specifically described below with reference to the example.

An alloyed hot-dip galvanized steel sheet having a sheet thickness of 0.8 mm was skin-pass rolled, so that top portions of convex portions in unevenness of the alloy layer surface were crushed to form flat portions. The resulting steel sheet was dipped for 1 second into a sulfuric acid acidic aqueous solution including 20 g/L of sodium acetate and exhibiting pH of 2.0 at a solution temperature of 50° C. After standing for a predetermined time, washing with water and drying were performed so as to produce 35 test samples in which an oxide (including hydroxide) mainly containing zinc was formed on the plating surface. The surfaces and backs of these steel sheets were used for the measurement of oxide film thicknesses. At this time, the standing time was changed within the range of 2 to 60 seconds and, thereby, the thickness of the oxide film formed on the flat portions of the plating surface of the test sample was adjusted. The thus produced test sample was stamped to have a diameter of 48 mm. Thereafter, ultrasonic cleaning was performed with toluene for 2 minutes and with ethanol for 1 minute. The resulting sample was dried with warm air and was set in a sample holder of the FX apparatus.

For the FX apparatus, Model ZSX101e fluorescent X-ray analyzer produced by Rigaku Industrial Corp., was used. The voltage and the current of the tube during the measurement were 30 KV and 100 mA, respectively, and the analyzing crystal was set to be TAP so as to detect the O-Kα x-ray. The pulse-height analyzer was set at an optimum value of the O-Kα x-ray in a manner described in one aspect. In the measurement of the O-Kα x-ray, the intensity was also measured at a background position, besides the peak position thereof, so that the net intensity of O-Kα x-ray was able to be calculated. Each of the integration times at the peak position and the background position was set at 20 seconds.

Silicon wafers provided with silicon oxide films, which had thicknesses of 96 nm, 54 nm, and 24 nm and which had been cleaved into appropriate sizes, were set on a sample stage together with the above-described series of samples, so that the intensity of O-Kα x-ray was able to be calculated from these silicon oxide films as well. A calibration curve between the oxide film thickness and the intensity of O-Kα x-ray was prepared by using these data, and the thickness of the oxide film of the test sample was calculated as the oxide film thickness value in terms of silicon film.

The oxide film thickness of the test sample was measured as described above and, subsequently, the friction coefficient thereof was measured by a flat die sliding test as a means for evaluating the press formability of the test sample. In the flat die sliding test, the test was performed by pressing a bead tool against a surface of the galvanized steel sheet fixed to a slide table with a pressing force of 400 Kgf and moving the slide table at the sliding speed of 100 cm/min so as to cause sliding between the galvanized steel sheet and the bead. Each of the bead-pressing load N and the slide table movement force F at this time was measured by using a load cell, and the friction coefficient during sliding was determined from the ratio of them (F/N). The surface to be measured was coated with a washing oil (R352L produced by PRETON) in advance. The contact surface of the bead with the steel sheet was a plane having a width of 10 mm and a length in the sliding direction of 3 mm. The thus determined friction coefficient mainly incorporates the sliding property of the bead portion during the press forming. Therefore, it can be judged that as the value of friction coefficient becomes smaller, the sliding resistance of the bead portion is small and breakage or the like does not occur easily during press forming.

Figure 5:
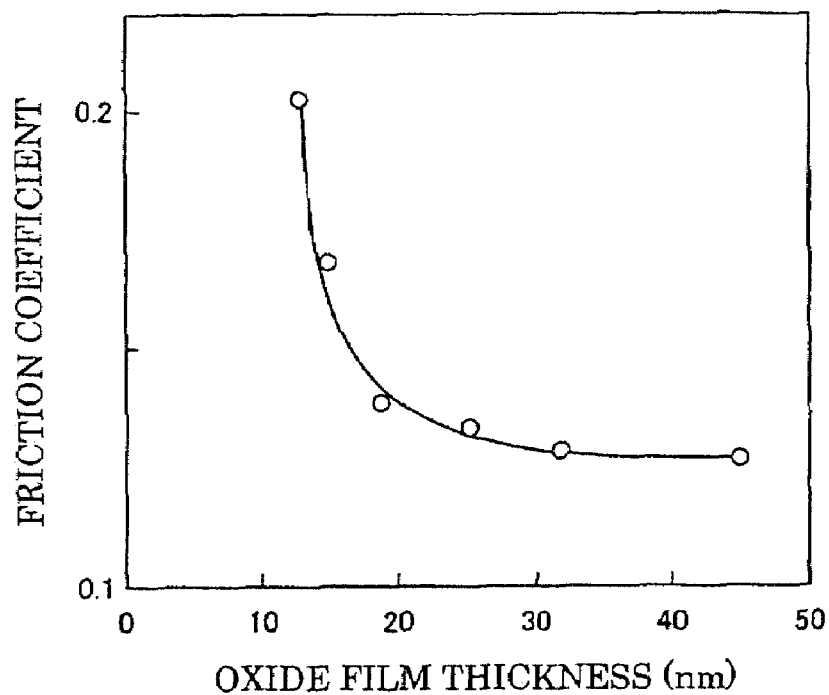
FIG. 5 is a diagram showing the correlation between the oxide film thickness and the friction coefficient of an alloyed hot-dip galvanized steel sheet.

FIG. 5 shows the relationship between the oxide film thickness and the friction coefficient measured as described above. As is clear from FIG. 5, there is a good correlation between the oxide film thickness and the friction coefficient. As the oxide film thickness increases up to about 20 nm, the friction coefficient decreases significantly. Therefore, the friction coefficient can be evaluated by controlling the thus measured oxide film thickness, where the friction coefficient is an important factor in the press formability of the alloyed hot-dip galvanized steel sheet. Furthermore, the level of the press formability can be judged by setting a threshold value of the friction coefficient in consideration of the press formability.

INDUSTRIAL APPLICABILITY

Our methods can be used for nondestructively speedily evaluating the press formability of a galvanized steel sheet including an oxide film having a thickness of 10 nm to 100 nm as a plating surface layer.

The invention claimed is:

1. A method for evaluating the press formability of a galvanized steel sheet, comprising the steps of:
    irradiating X-rays to a galvanized steel sheet, which is a sample to be measured;
    dispersing a fluorescent X-ray, which is excited and emitted in the irradiating step, with an analyzing crystal exhibiting a difference in diffraction angle between a primary oxygen Kα x-ray and a secondary zinc Lβ x-ray of 2 degrees or more;
    detecting the fluorescent X-ray, which is dispersed in the dispersing step and which mainly contains the primary oxygen Kα x-ray, with a detector;
    separating an X-ray portion from the fluorescent X-ray at an energy level within the range of ±25% to ±75% relative to a reference that is the energy level of the primary oxygen Kα x-ray, which is detected in the detecting step and which mainly contains the primary oxygen Kα x-ray, by adjusting a window width of a pulse-height analyzer;
    measuring the intensity of the X-ray portion separated in the separating step; and
    evaluating the press formability of the galvanized steel sheet on the basis of the intensity of the X-ray measured in the measuring step.

2. The method according to claim 1, further comprising the steps of:
    preparing a calibration curve representing a relationship between the intensity of primary oxygen Kα x-ray and an oxide film thickness using silicon oxide films with known thickness formed on mirror polished silicon wafers; and
    calculating a thickness of an oxide film formed on the galvanized steel sheet by using the calibration curve from the intensity of the X-ray measured in the measuring step and wherein the press formability of the galvanized steel sheet is evaluated on the basis of the calculated film thickness.

3. A method for evaluating press formability of a galvanized steel sheet comprising:
    irradiating a galvanized steel sheet with X-rays;
    dispersing a fluorescent X-ray, which is excited and emitted, with an analyzing crystal exhibiting a difference in diffraction angle between a primary oxygen Kα x-ray and a secondary zinc Lβ x-ray of 2 degrees or more;
    detecting the dispersed fluorescent X-ray, which mainly contains the primary oxygen Kα x-ray, with a detector;
    separating an X-ray portion from the fluorescent X-ray at an energy level within the range of ±25% to ±75% relative to a reference that is an energy level of the detected primary oxygen Kα x-ray, which mainly contains the primary oxygen Kα x-ray, by adjusting a window width of a pulse-height analyzer;
    measuring intensity of the separated X-ray portion; and
    evaluating the press formability of the galvanized steel sheet on the basis of the intensity of the measured X-ray.

4. The method according to claim 3, further comprising the steps of:
    preparing a calibration curve representing a relationship between the intensity of primary oxygen Kα x-ray and an oxide film thickness using silicon oxide films with known thickness formed on mirror polished silicon wafers; and
    calculating a thickness of an oxide film formed on the galvanized steel sheet by using the calibration curve from the intensity of the x-ray measured in the measuring step, and wherein the press formability of the galvanized steel sheet is evaluated on the basis of the calculated film thickness.

* * * * *